United States Patent [19]

Savoy

[11] Patent Number: 5,270,108

[45] Date of Patent: Dec. 14, 1993

[54] BUILDING MATERIAL WITH PROTECTION FROM INSECTS, MOLDS, AND FUNGI

[75] Inventor: Thomas L. Savoy, Prior Lake, Minn.

[73] Assignee: AFM Corporation, Excelsior, Minn.

[21] Appl. No.: 458,168

[22] Filed: Dec. 28, 1989

[51] Int. Cl.⁵ .............................. B32B 3/26; C08J 9/16
[52] U.S. Cl. ............................... 428/305.5; 418/317.9; 418/318.4; 418/907; 521/54; 521/55; 521/56
[58] Field of Search ............... 428/305.5, 314.2, 317.1, 428/317.7, 907, 317.9, 318.4; 521/55, 54, 56

[56] References Cited

U.S. PATENT DOCUMENTS

| | | | |
|---|---|---|---|
| 1,620,587 | 3/1927 | Williamson | 124/409 |
| 2,186,134 | 1/1940 | Chapman et al. | 424/658 |
| 3,473,252 | 10/1969 | Kramer | 43/124 |
| 3,619,437 | 11/1971 | McDonald, Jr. | 264/46.6 |
| 3,816,610 | 6/1974 | Lusby | 424/17 |
| 4,438,090 | 3/1984 | Brite | 424/7.1 |
| 4,461,758 | 7/1984 | Brite | 424/10 |
| 4,564,554 | 1/1986 | Mikuski | 428/318.4 |
| 4,576,801 | 3/1986 | Parry et al. | 427/288 |
| 4,587,164 | 5/1986 | Freeman | 428/318.4 |
| 4,648,202 | 3/1987 | Renth | 43/132.1 |
| 4,688,349 | 8/1987 | Renth | 43/132.1 |
| 4,807,391 | 2/1989 | Bokiau | 43/131 |
| 4,826,682 | 5/1989 | Sakharova | 424/623 |
| 4,942,084 | 1/1990 | Prince | 428/318.4 |

OTHER PUBLICATIONS

TIM-BOR for Wood Preservation-Treatment Manual United States Borax & Chemical Corporation.

*Primary Examiner*—George F. Lesmes
*Assistant Examiner*—Blaine Copenheaver
*Attorney, Agent, or Firm*—Wm. Bruce Day

[57] ABSTRACT

An insulated building panel for use in residential or commercial construction comprising a core of expanded polystyrene (EPS) bonded to at least two exterior skins of oriented strand board by a urethane laminating adhesive and treated with a sodium borate, such as disodium octaborate tetrahydrate, to preserve and protect the building panels from attack by many types of insects, molds, and fungi is disclosed. In an alternative embodiment, EPS for a variety of construction and insulating uses so protected are disclosed.

9 Claims, 1 Drawing Sheet

BUILDING MATERIAL WITH PROTECTION FROM INSECTS, MOLDS, AND FUNGI

BACKGROUND OF THE INVENTION

1. Field of the Invention

The present invention is directed to laminated building panels with protection from insects, molds, and fungi. More particularly, the present invention is directed to building panels comprising a sandwich of two skins bonded to a core of a firm solid insulating material, or the insulating material itself, that is protected against attack by many types of insects, molds, and fungi.

2. Description of the Related Art

Pests such as termites, carpenter ants, insects, and so forth have long been a scourge of wooden buildings. Extensive efforts to control insect infestation of buildings have been undertaken. Many chemical preparations for exterior application to a building or foundation have been developed. Many of these chemicals are also hazardous to pets and humans and have consequently been banned.

For example, creosote has long been used to preserve wood and is now unavailable for residential use because creosote is carcinogenic.

Copper-chrome-arsenate (CCA) solutions have long been used to treat wood under high pressure and comprise the majority of treated wood now available. CCA treated wood is, however, highly insecticidal and fungicidal and must be handled with considerable extraordinary care.

One such effort to develop a preservative to deter insect and vermin infestation is found in U.S. Pat. No. 2,186,134, issued to Chapman on Jan. 9, 1940. Chapman discloses the use of a preservative composition comprising a halogenated phenol and an alkali metal salt of boric acid in an aqueous solution which is applied to fiber based building materials such as fiberboard, insulation made of paper and so forth. Engineered materials unknown to Chapman now comprise an important portion of the available range of building materials. One such example is the prefabricated insulated building panels comprising a core of expanded polystyrene (EPS), which may be about 3½–11½ inches (8.9–40 cm) thick, sandwiched between two wood-based sheets or other skins, such as metal. The panels may be in any convenient size, with the most popular size being about 4 feet by 8 feet (1.2 m × 2.4 m). The wood-based panels, may be tempered hardboard, chipboard, particleboard, oriented strand board, and the like. The two skins are each typically at least ⅜ inch (0.95 cm) thick when the panels are intended to form load bearing walls. The panels are adhesively bonded by a urethane laminating adhesive. Such prefabricated building panels have become extremely popular because they provide high insulation value, and virtually eliminate drafts through the roofs, walls and floors. They provide economical alternatives to stick-built structures in part by reducing the framing time of the construction of a new home or other buildings by about two-thirds.

It has been found, however, that in some situations such panels may be attacked by insects, molds, or fungus. Insects may bore through the oriented strand board or waferboard into the expanded polystyrene core (EPS), where they may nest. The environment within the core of the building panel provides good living conditions for most insects since it is usually warm during the winter, cool during summer and non-toxic. Conventional chemical treatments may be applied to prevent such attacks in the same fashion as they are applied to other wood-based structures. Regular application of such chemicals, however, is expensive and inconvenient. In addition, such chemicals may well be significantly toxic to humans and pets.

Accordingly, there is a need for an energy efficient laminated building panel that resists attack by insects, mold and fungus.

SUMMARY OF THE INVENTION

Accordingly, it is a primary object of the present invention to provide an energy efficient laminated building panel that resists attack by insects, mold and fungus.

These and other objects of the present invention are achieved by providing a building panel comprising at least two spaced-apart lamination skins, such as wood-based skins and a core of firm, solid insulating material laminated between the skins. The sandwich is held together by suitable adhesives, such as a urethane laminating adhesive. A chemical composition of matter having insecticidal and fungicidal properties without major toxicological problems is diffused through and permeates at least a portion of the skins and core. Alternatively, the core, which is formed prior to fabrication of the building panel, may be made from polystyrene beads mixed with a suitable chemical prior to expansion into a solid core by conventional means. The treated core may then be laminated with separately treated skins. In an alternative environment, EPS so treated, whether formed into blocks or loose fill, finds many construction and insulating applications as a separate building material without any lamination to skins or other material.

Preferably the insecticidal and fungicidal chemical will be highly insecticidal and fungicidal to many types of insects, mold and fungus, but will not be significantly insecticidal and fungicidal to pets, other large animals, or humans. In addition, the chemical should not migrate, but remain in the building panel or EPS indefinitely. It has been found that certain borates meet these criteria More particularly, disodium octaborate tetrahydrate embodies these desirable characteristics and is the preferred primary chemical for treating building panels or EPS according to the present invention.

The panel skins may be wood-based and may comprise plywood, wafer board, particleboard, tempered hardboard, and the like. In the preferred embodiment, oriented strand board is employed for the skin because it is highly resistant to warping and exhibits good compression strength.

The core of the building panel consists of a rigid firm foam insulating material, with the preferred material comprising expanded polystyrene, or other foam.

Several processes for making a building panel protected against insect pests have been developed. Perhaps most effective is mixing the borate having insecticidal and fungicidal properties with the polystyrene from the plastics manufacturer prior to expanding the polystyrene and borate mixture into a mold to produce the expanded polystyrene. The molded EPS, now protected against many types of insects, molds and fungi, can be put to many uses. For example, the EPS blocks may be used as perimeter insulation and underslab insulation to stop or reduce energy loss at the foundation and slab of a building, such as a house. The expanded EPS, now treated for protection against insects, molds, and fungi, is stable and has a very low moisture gain. It is available in a variety of densities for higher insulation value and compression resistance. The treated EPS may also be used for exterior sheathing to create an energy loss barrier for any frame type construction in both new and rehab applications. EPS can be used for cavity fill and may be manufactured in the desired sizes prior to treatment, or cut to size in the field and given a supplemental field treatment prior to installation or filling cavities such as spaces between joists. The treated EPS also serves as an excellent siding backer, eave vents, frame fill, and drywall backer In all these applications, the treated EPS increases the energy efficiency and sound absorption characteristics of the building, as well as reducing significantly the threat of infestation by insects, molds, or fungi. In the aforementioned uses, the EPS is in the form of a firm, solid block of EPS. In alternative embodiments, however, the EPS may be in the form of peanut-shaped individual pellets, loose expanded beads, or other forms of loose fill material. Alternatively, the treated EPS can be laminated between two skins to form building panels, the skins may be metal, plastic, wood and the like. The skins may have been previously treated by the borate, or may be treated after the panel has been laminated.

In an other process, the entire building panel is constructed and then treated with a borate having insecticidal and fungicidal properties. The panel may be treated by dipping or immersing it into an aqueous solution of the borate, by spraying the solution onto the panel, e.g., by passing the panel through a spray tunnel, by pressure treatment, by the hot and cold bath process, or other methods.

In alternative embodiment of the process, the core is formed of expanded polystyrene and then is treated according to one of the methods described immediately above. The skins are treated separately according to one of the methods cited above. The skins may be treated in a different time and a different place from the core, but after both are separately treated they are united by laminating the core between at least two skins and bonding the unit with a suitable adhesive, such as a urethane laminating adhesive, to form the building panel.

Other objects and advantages of this invention will become apparent from the following description taken in conjunction with the accompanying drawings, wherein is set forth by way of illustration and example, the preferred embodiments of this invention.

DETAILED DESCRIPTION OF THE PREFERRED EMBODIMENTS

As required by the statutes and case law, a detailed embodiment of the present invention is disclosed herein. It is to be understood, however, that the disclosed embodiment is merely exemplary of the invention, which may be embodied in many various forms. Therefore, the specific structural and functional details of the invention as disclosed herein are not to be interpreted as limiting, but merely as a basis for the claims and as a representative basis for teaching one skilled in the art to variously employ the present invention in virtually any appropriately detailed structure.

Figure 1:
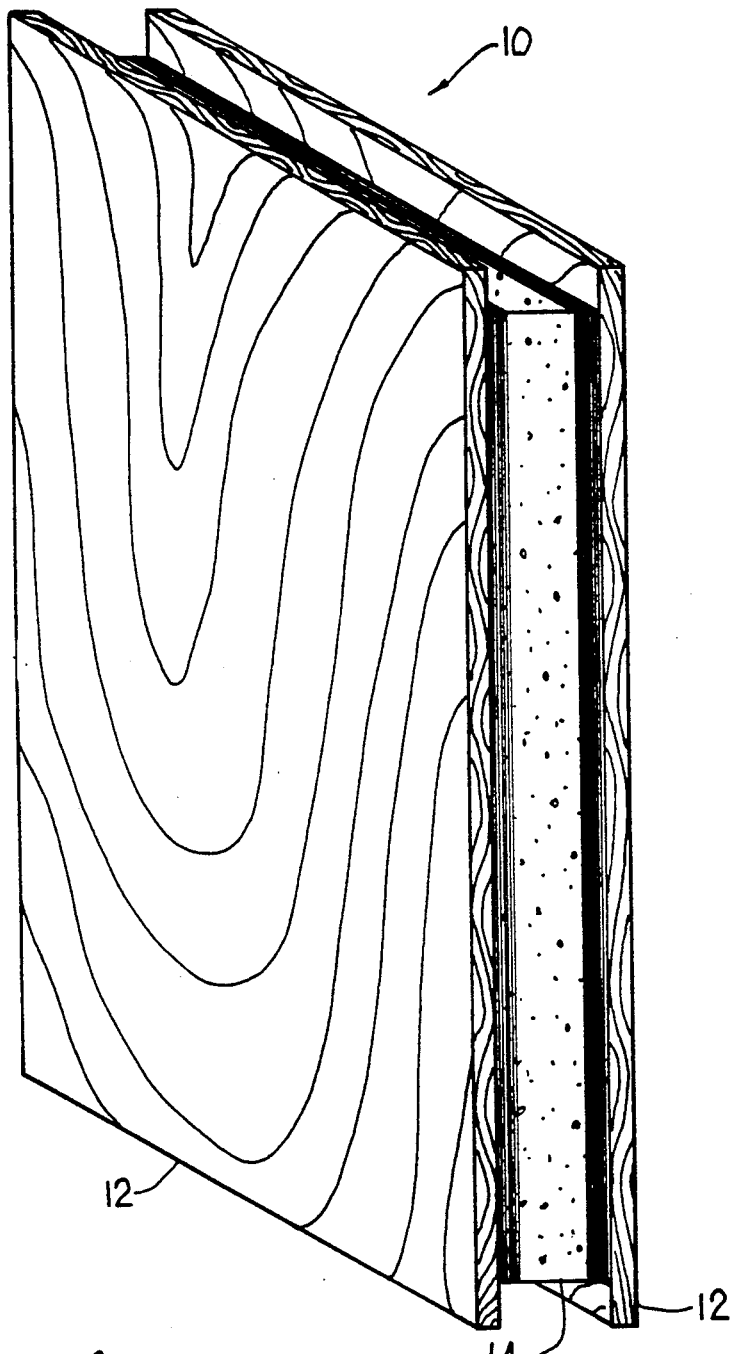
FIG. 1 is a perspective view of a building panel according to the present invention.
Figure 2:
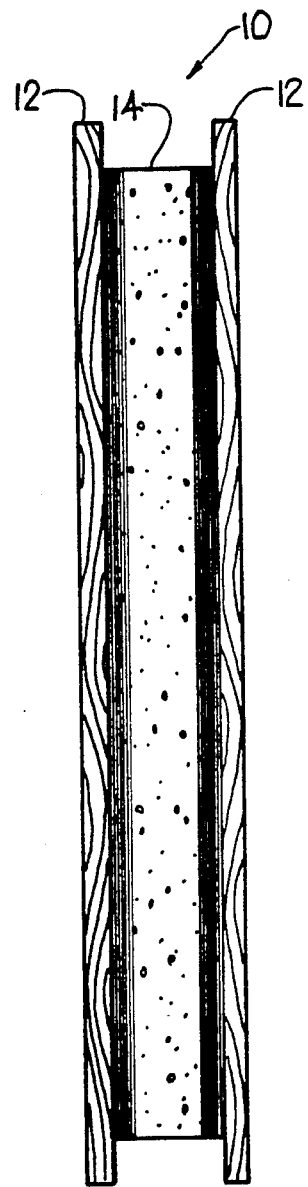
FIG. 2 is an end elevation of the building panel of FIG. 1.

Referring to FIG. 1, the laminated building panel with protection from insects, molds, and fungi 10 disclosed herein comprises a central the core 14 of $3\frac{1}{2}$–$11\frac{1}{2}$ inches (8.9–40 cm) of a firm solid insulating material, e.g., such expanded polystyrene foam, or other foam material, which may be a chemical foam material. The core 14 is laminated between at least two skins 12, which are preferably wood-based skins of waferboard or oriented strand board, although they may also be chipboard, particleboard, tempered hardboard, and the like. In the preferred embodiment, the core is of a solid rectangular shape and two skins are employed, one on each of large flat surface of the core. The skins are bonded to the core by an adhesive 16, such as a urethane laminating adhesive.

The panel 10 is treated with a chemical highly insecticidal and fungicidal to many insects, molds and fungi but not significantly toxic to household pets, other large animals, and human beings to prevent insects from boring through the skins and nesting in the core, from which they may migrate into the structure. It has been found that certain borates, particularly a sodium borate, meet these criteria, and in particular disodium octaborate tetrahydrate has been found useful in such applications. Sodium borates kill many pests in addition to discouraging them from attacking the treated building panels 10.

The panels may be treated with disodium octaborate tetrahydrate and related chemicals either prior to or following construction of the materials into a panel. A variety of processes may be employed as described below.

A. Treatment Chemicals.

In general, building materials such as the panels 10 or plain EPS may be treated by any of a number of processes, all or any of which may be used to treat the materials of the building panels 10 or the EPS either prior to or following lamination. The preferred embodiment of the treatment chemicals and the various preferred processes are described.

Borates are either salts or esters of boron. In particular, disodium octaborate tetrahydrate ($Na_2B_8O_{13}4H_2O$) which may have a typical chemical analysis of sodium oxide ($Na_2O$) 14.7 percent; boric oxide ($B_2O_3$) 67.1 percent; and water of crystallization ($H_2O$) 18.2 percent is particularly effective in eliminating the threat of damage from many types of pests notably many boring insects. The disodium octaborate tetrahydrate may comprise 99.4 percent of the total chemical content of the treatment chemical, with impurities and other inert ingredients comprising the remaining 0.6 percent of the treatment chemical. The minimum borate oxide ($B_2O_3$) content of the treatment chemical should be in a range from about 50 percent to about 70 percent, with the optimal proportion being about 66.1 percent. A preservative so constituted is not considered harmful to human beings or livestock. It can be handled by workmen without the need to observe any special precautions. Further, there is no danger to health in preparation or use of solutions of the treatment chemical or in the handling and milling of construction materials treated with this treatment chemical. The treatment chemical has no objectionable odor and has nearly a neutral pH factor. In timber, the salt retention is about 0.3 pounds per cubic foot, which is very low compared with the total weight of the timber. In foam, the salt retention rate may be somewhat less. The solution of the treatment chemical water is non-corrosive to ferrous metals, but may attack aluminum. The treatment chemical has no effect on plastics, cements, rubber, putties, bituminous solutions, mastics or other sealants.

Diffusion of the treatment chemical throughout wood, in particular, timber, depends on a number of characteristics, including the moisture content of the material, the concentration and temperature of the treating solution, the curing and diffusion storage conditions, and so forth. Most important among these factors for timber is the moisture content. A moisture content of wood or timber of greater than 40 percent based on oven dry wood weight is recommended for complete diffusion. This is because the primary vehicle for diffusing the treatment chemicals throughout the lumber is osmosis, which causes the salts to become equally concentrated throughout the wood by passage of the solvent, i.e., the water, of the less concentrated solution through the membranes of the timber toward the more concentrated solution. Timber and wood, being cellulose designed for drawing moisture, are highly amenable to chemical treatment by aqueous solutions, because osmosis will distribute the treatment chemicals.

EPS is comprised of essentially noncommunicating air-filled cells, not the long grain structure that allows timber to draw moisture. The actual EPS is a non-porous and has no cell wall or membrane for diffusing chemicals through osmosis. Accordingly, the diffusion mechanism used for treating wood is unavailable for treating EPS.

A molded EPS, however, has a multitude of small interstitial spaces. It is believed that these interstitial spaces allow for the capillary uptake of the treatment solution by the EPS and that complete diffusion throughout the EPS block or the core 14 can be attained. It has also been found, however, that complete diffusion is not required for good preservative protection in the building panels 10 or the EPS because few, if any, field cuts that would expose untreated cross sections of the building panels 10 or the EPS are made. When such field cuts are made, such as for windows, the exposed cross sections can be field treated and then can be covered with other material, such as headers, jams, sills, and so forth, which may be of treated building material if desired.

Diffusion of the treatment chemicals throughout all or a portion of the skins 12 or the core 14 of a building panel 10, or of an EPS building material can be effected through a number of processes for application of the treatment chemicals, some of which are discussed below, with the treatment steps being clearly set forth.

B. Treatment Processes.

1. In the momentary immersion process, the building material is immersed in a solution of the treatment chemical and water for a period of 2-5 minutes. After this soaking, the panel is tilted so that excess preservative can be drained off. Then the moist panel, or other construction materials, are moved to a storage area to allow the diffusion process to proceed. A plurality of building panels 10 may be stacked with suitable spacers between the panels prior to dipping if desired (stickering).

2. In the spray tunnel process, individual building panels 10, or cores 14, are passed on rollers through a tunnel fitted with jets or a broad fan nozzle. Hot concentrated treatment aqueous solution is pumped from a tank through the piping and sprayed onto the building panel 10 or the the EPS, or the core 14. The treatment solution that falls to the bottom of the tank is collected and recirculated. It is run through a filtering system to remove sawdust and other suspended material from the circulating solution. For treatment of many laminated building panels 10, a concentration of 150-350 pounds (68-169 kg) of treatment chemical per 100 gallons (377 l) of solution at 120° F.-140° F. (60°-67° C.) is recommended to maximize the penetration of the treatment chemicals into the building panel 10. Lesser concentrations may result in adequate protection.

3. In yet another method, the spray treatment process, the treatment chemical can be sprayed onto the building panel 10 at a temperature of approximately 100° F. (56° C.) with an electric or pneumatically driven pump sprayer. Proper storage for diffusion allows adequate protection with this method.

Following coating of the building panels 10, or other building materials, such as the EPS, the core 14 or the skins 12, the treated materials are stacked and can be covered with polyethylene sheeting or other vapor barrier, if desired, to reduce or eliminate air movement around and within the stack of materials and provide an improvous barrier to rain water. The polyethylene sheeting, if used, slows evaporation and allows the diffusion of the treatment chemical into the building materials to continue. If the wet panels 10 are covered with a vapor barrier for more than about 2 days, however, they may warp.

4. In the pressure treatment method, it is possible to use the treatment chemical with a conventional pressure treatment method commonly associated with preservatives such as creosote and copper-crome-arsenate (CCA) solutions. The precise parameters of the pressure treatment system will be determined by the characteristics of the building material being treated, but should result in a retention of about 0.3 pounds per cubic foot (4.8 kg. per cubic meter) of the treatment chemical in the assay zone. The concentration of the treatment solution must be adjusted to give the correct retention. It is noted, however, that solutions are in the range of 1-2 percent (0.1-0.2 pounds per g/l)(12-24 gallon). For pressure treatment, the building material should be dried to less than 25 percent moisture as oven dry weight and stickered prior to treatment.

The processes described above in numbered paragraphs 1, 2, 3, and 4 can be applied to the completed building panel 10, or to the skins 12 to plain EPS, or the core 14 separately. The flexibility in applications of the processes allows for the use of pre-treated skins 12, which naturally may be provided by an outside vendor or prepared during the process of manufacturing the entire panels.

When the entire laminated panel 10 is treated after its manufacture, it must be stored for curing in a fully supported flat shape. A minimum curing period of at least 1 day, during which the material need not be covered with a vapor barrier, is required to assure lamination. Preferably, a plurality of the panels 10 is wet stacked, and allowed to cure for 3 days.

If the skins 12 and the EPS, or the core 14 are treated separately, another embodiment of the treatment process is preferred. The skins 12 are to be treated as described above. The EPS, or the core 14 may be treated as described above or the treatment chemicals may be incorporated in a dry powder form into the core during its formation.

5. The simultaneous formation of expanded polystyrene with a sodium borate preservative process. Expanding polystyrene is a well known art. Polystyrene is commercially available in small, irregular beads. Expanded polystyrene is made by pouring the polystyrene beads into a hopper, from which they fall by the force of gravity into a heating chamber where they are heated with steam and forced along an air conveyor while subject to the heat and moisture of the steam, which causes the beads of polystyrene to expand. The beads expand continuously throughout their travel along the air conveyor and into the mold, or blank. The polystyrene beads become hot and tacky and, as they cool, they adhere to one another. Only sufficient pressure to cause the expanded polystyrene beads to stick together is applied. Too much pressure would crush the foam beads and reduce their insulating value. Expanded polystyrene can be formed in molds to any convenient size, such as 4 feet by 8 feet by 5 inches (1.2×2.4×0.127 m), which is a useful size in the present application. In the preferred embodiment for separately treated skins 12 and cores 14, the treatment chemicals, consisting primarily of disodium octaborate tetrahydrate in powdered form, are added to the polystyrene beads and the two ingredients are mixed together prior to expansion of the polystyrene beads by the steam. In this process, the treatment chemicals are added to the polystyrene beads in sufficient concentration to allow a retention of the treatment chemical of 0.3 pounds per cubic foot (4.8 kg. per cubic meter). In a typical sheet of the EPS, or the core 14 material having the dimensions 4 feet by 8 feet by 5 inches (1.2×2.4×0.127 m), treatment chemicals would be added in the range of about 3.0–4.1 pounds (1.77–1.8 kg), with an ideal amount, assuming thorough mixing and the goal of providing a largely homogenous dispersion of the treatment chemical throughout the EPS, or the core 14 in the desired high concentration, of about 3.9 pounds (1.77 kg). EPS is conventionally manufactured in thicknesses up to about 2 feet (0.6 m). To obtain the desired extent of penetration into such blocks, it may be desired to subject the EPS to pressures greater than 1 atmosphere, and to continue the treatment for a greater time than with thinner blocks of EPS. For equal degrees at penetration and protection, the desired ratios of the treatment chemicals to the volume of EPS being treated remain the same.

Following such treatment, the EPS, or the core 14, now infused with treatment chemicals is allowed to cool, is removed from the mold stored fully supported and flat, and allowed to cure for at least 1 day, preferably 3. Curing times and temperatures may be adjusted as desired in accordance with schedules set forth previously. Aging in ambient indoor conditions to promote slow dehydration is preferred. When the the EPS, or the core 14 is satisfactorily cured. Then the building panel 10 can be fabricated as described above, by laminating the two skins 12 on either side of the EPS core 14 with a suitable adhesive, such as a urethane laminating adhesive, or in general construction uses.

C. Testing the Penetration of the Treatment Chemicals.

The penetration of the treatment chemicals into the building panels 10 and EPS can be checked by a chemical test applied to a cross section of the treated material. The testing procedure requires cutting thin cross section about ¼ to 1 inch (0.63–2.54 cm) thick (15 cm) from the end of the treated material with a fine-tooth saw. The section is then dried in an oven at a temperature not to exceed 140° F. (60° C.) for 2-3 hours. Then a 10 percent alcoholic extract of curcumin is applied in a fine uniform spray to the sample and allowed to dry. Then a solution of 6.0 grams salicylic acid in 20 ml of concentrated hydrochloric acid and then diluted to 100 ml with ethanol is similarly sprayed onto the sample and allowed to dry a few minutes. Any resulting color changes in the sample should be observed and assessed 10-15 minutes after application of the second solution. The color graduation from the surface of the sample to the center of the cross section of the sample indicates the extent of penetration of the treatment chemicals. The color turns red where the treatment chemicals are present.

Quantitative analysis can also be carried out to determine the amount of treatment chemicals that have become embedded in the treated building materials, if desired.

D. Tests of Effectiveness.

Numerous independent tests of the effectiveness of the treatment methods described above have been conducted on samples of the building panels 10. They are described below.

EXAMPLE ONE

The purpose of this test was to monitor the effective penetration of various solutions of a sodium borate, namely disodium octaborate tetrahydrate in a post lamination application to the building panels by utilizing the colorimetric test described above. Eight samples 6 inches by 6 inches by 4¼ inches (15×15×11.5 cm) of the building panels were obtained including a 3⅝ inch (92 cm) expanded polystyrene core with 7/16 inch (1.11 cm) skins. Other core thicknesses and skin thicknesses may be substituted if desired Two solutions of the treatment chemicals were prepared, the first consisting of 3.2 pounds (1.45 kg) of the treatment chemicals to 1 gallon (3.77 l) of hot water (130° F.; 72° C.) and the second solution of 1.8 pounds (5.5 kg) of the treatment chemicals to 1 gallon of hot water (130° F.) (72° C.). The solutions were separately mixed thoroughly and placed in separate labeled hand-held pump sprayers. Sprayers were immersed into a hot water (130° F.; 72° C.) bath until use.

Each solution was vigorously shaken for 1 minute immediately prior to spraying all sides of the four labeled samples. The solution was applied in sufficient quantity that the solution ran off the samples. The wetted samples were placed on a drying rack for 1 week at ambient drying conditions. After drying, the panels were dissected to obtain cross sections of ¼ inch 0.635 cm), ½ inch( 1.27 cm), and 1 inch (2.54 cm) in thickness, using a fine bladed saw. They were tested according to the colorimetric described above, with a 10 percent alcoholic extractive curcumin solution and allowed to dry. Then a fine mist of a solution of 6.0 grams salicylic acid and 20 ml. concentrated HCl diluted to 100 ml. with ethanol was sprayed onto the samples and the color of the samples 10 minutes, 15 minutes, and 30 minutes after treatment were recorded. These tests showed a deep red color on the interior face of all cross sections. The red color was noted on both the core 14 and the skins, indicating penetration and diffusion of the sodium borate throughout the entire building panel 10.

EXAMPLE TWO

Six samples having to dimensions of 6 inches by 6 inches by 4½ inches (15×15×11.5 cm), and including a 3⅝ inch (9.2 cm) expanded polystyrene core and 7/16 inch (1.11 cm) wafer board skins on both sides of the core was sprayed using a hand-held pump sprayer with a single solution of 2 pounds (0.90 kg) of treatment chemicals dissolved in 1 gallon (3.77 l) of water at 130° F. (72° C.). The pump sprayer containing the solution was placed in a hot water bath (130° F.; 72° C.). Prior to spray application, the solution was vigorously agitated for 1 minute to maximize dissolution of the treatment chemicals and hold any undissolved treatment chemicals in suspension. The application rate was approximately 200–250 square feet per gallon (4.9–6.1 square meters per liter). Three of the samples were treated in this matter and were subjected to native Eastern subterranean termites, *Reticulitermes flavipes* (Kollar). The termites were killed very quickly in the test, which was conducted as follows.

A 1,600 gram layer of moist sand and vermiculite mixture was placed in each of six 5 gallon (18.55 l) lard containers with lids as a substrate for termites. The approximate mixture of the substrate was: 363 grams vermiculite; 3,584 grams of sand, and 1,670 grams water (that is, 3 parts of sand to 3 parts of vermiculite by volume). A brick sterilized by heating in an oven was placed in each substrate layer to support the panel sample above the moist substrate.

Counts of termites in the three 1 gram samples of termites averaged 691 termites, therefore 14.4 grams (4,975 live termites) of Reticulitermes flavipes termites of mixed castes were placed in each can on Mar. 24, 1989 after collection two days earlier from naturally infested dead southern pine logs.

The exposure was ended on Apr. 7, 1989 because all the termites in the treated building panels 10 were dead. It further appeared that these termites had been dead after only one week of exposure to the treated building panel samples. Closer examination revealed that 3 preadults (adult termites), 11 soldiers; 33 prealates, and 3 soldiers and 16 prealates, survived in the respective three samples. All survivors are non-feeding forms of termites that apparently did not receive sufficient insecticidal and fungicidal before all the workers died. These forms of termites will die from starvation in the absence of workers. At the same time, the termites exposed to the untreated panels remained healthy.

Thirty-two samples of building control panels measuring 12 inches by 12 inches by 4½ inches (30.5×30.5×11.4 cm) and including a 3⅝ inch (9.2 cm) expanded polystyrene core laminated to 7/16 inch (1.11 cm) wafer board skins and including a horizontal electrical chase and a vertical electrical chase, both measuring 1½ inches (3.8 cm) in diameter located in the center of the samples was treated as described in example two above, with the spray being applied by a common hand-held garden sprayer.

These samples were subjected to two large colonies each of *Camponotus modoc* and *C. vininus* (carpenter ants) collected in the wild in the Moscow mountains near Viola, Idaho and were placed in garbage cans with a rim lining of petroleum jelly mixed with mineral oil to prevent escape. Sets of five treated or untreated sample panels were placed in each of the four carpenter ant colonies. Water and honey dishes were placed on the top panels of the cans. The panels were observed at intervals to determine the rate of ant chewing and death due to the treatment.

On Aug. 18, 1989 the ants were placed with the panels. By the next day the *C. modoc* colony had started to chew into the polystyrene cores of the control panels, i.e., the untreated panels. On August 28, the *C. vininus* had started chewing into the control panels and the *C. modoc* had excavated more tunnels. No chewing occurred in either of the panel sets that had been treated with the treatment chemicals, and dead ants were seen on the bottoms of the garbage cans. On September 4, about 95 percent of the *C. modoc* in the treated panels were dead, with no chewing on the polystyrene. About 70 percent of the *C. vininus* were also dead without any chewing. All but a few of the *C. modoc* and the *C. vininus* with the treated panels were dead by September 10. Conversely, the untreated panels were heavily burrowed by the *C. modoc*, although not by the *C. vininus*. In conclusion, the treatment was effective and worked fairly quickly, and seems to have deterred the ants from chewing as well as killing them.

EXAMPLE THREE

The purpose of this example was to monitor the effect, if any, of the chemical treatments described herein on the bond strength of the treated building panels by treating them with a sodium borate, such as disodium octaborate tetrahydrate and then using the AFM Tension Test. In particular, three samples of building panel having dimensions 6 inches by 6 inches by 4½ inches (15×15×11.5 cm), including a 3⅝ inch (9.2 cm) expand of polystyrene core with 7/16 inch (1.11 cm) oriented strand board (OSB) skins secured by a suitable urethane laminating adhesive were treated with the treatment chemicals. A solution of 2 pounds (0.90 kg) of treatment chemicals to 1 gallon (3.77 l) of hot water (130° F.; 72° C.) was prepared and thoroughly mixed and poured into a hand-held pump sprayer. The hot solution was applied directly via spray to all sides of the three samples in sufficient quantity that the solution ran off the samples. The wetted samples were placed on a drying rack for one week in abient conditions. Then they were placed in standard cardboard containers and allowed further aging for six months in an abient conditions. After six months of ambient storage they were subjected to a standard AFM R-Control Quality Control tension test, similar to a standard ASTM C-297. The tension test gauge readings were documented and the actual bond strength calculated. The samples determined in this test were:

|  | Gauge Reading | Tensile Strength |
| --- | --- | --- |
| Sample #1 | 404 PSIG | 23.6 lbs/in$^2$ |
| Sample #2 | 385 PSIG | 22.5 lbs/in$^2$ |
| Sample #3 | 385 PSIG | 22.5 lbs/in$^2$ |

These tensile strengths are the same as those of untreated building panels 10. Accordingly, it appears that the treatment regimen described in this example has no deleterious effects on the bonds between the waferboard, or skins, and the core of the building panel 10 that was present at the time of panel construction.

In operation, it is important that the treated building panels 10 not be exposed to excess moisture, or rain, after treatment. During transportation and storage of the building panels 10 therefore, they must be kept out of the rain to protect the chemicals. Building codes almost always require the skins 12 to be covered with another layer of building material. Interior walls must be covered with a 15 minute thermal index material, such as gypsum board, to meet fire code requirements. Exterior walls must be covered with sheathing or cladding, such as clapboards to meet building codes. The cladding or wallboard is then finished as desired by the consumer. These interior and exterior cladding materials protect the treated building panels 10 from rain and other elements. When the building panels 10 are kept dry by cladding or other means, the treatment is permanent, protecting the building panels 10 from many types of insects, molds, and fungi for the life of the structure.

While certain forms of this invention have been illustrated and described herein, the invention is not limited thereto, except insofar as such limitations are included in the following claims.

What is claimed as new and desired to be protected by Letters Patent is as follows:

1. A building material comprising:
   (a) expanded polystyrene; and
   (b) a treatment chemical comprised of a borate having insecticidal and fungicidal properties mixed throughout a least a portion of said expanded polystyrene.

2. A building material as claimed in Claim 1 wherein said expanded polystyrene is in the form of a firm solid block.

3. A building material as claimed in Claim 1 wherein said expanded polystyrene is in the form of small individual pellets.

4. A building material as claimed in Claim 1 wherein said borate further consists essentially of a sodium borate.

5. A building material as claimed in Claim 4 wherein said sodium borate consists essentially of disodium octaborate tetrahydrate.

6. A process for making a building material comprising the steps of:
   (a) mixing a borate having insecticidal and fungicidal properties with beads of a polystyrene; and
   (b) expanding said mixture.

7. A process as claimed in Claim 6 further comprising expanding said polystyrene into a mold.

8. A process for making a building material comprising the steps of:
   (a) expanding a polystyrene into a mold; and
   (b) treating said polystyrene with a borate having insecticidal and fungicidal properties.

9. A process as claimed in Claim 8 wherein said treatment step further comprises dipping said expanded polystyrene into a treatment solution.

* * * * *

US005270108C1

(12) EX PARTE REEXAMINATION CERTIFICATE (5805th)

United States Patent
Savoy

(10) Number: US 5,270,108 C1
(45) Certificate Issued: Jul. 10, 2007

(54) BUILDING MATERIAL WITH PROTECTION FROM INSECTS, MOLDS, AND FUNGI

(75) Inventor: Thomas L. Savoy, Prior Lake, MN (US)

(73) Assignee: AFM Corporation, Shorewood, MN (US)

Reexamination Request:
No. 90/006,811, Oct. 17, 2003

Reexamination Certificate for:
Patent No.: 5,270,108
Issued: Dec. 14, 1993
Appl. No.: 07/458,168
Filed: Dec. 28, 1989

(51) Int. Cl.
*B32B 3/26* (2006.01)
*C08J 9/16* (2006.01)

(52) U.S. Cl. ............... 428/305.5; 418/317.9; 418/318.4; 418/907; 521/54; 521/55; 521/56

(58) Field of Classification Search .............. 428/305.5, 428/317.9, 318.4, 907; 521/54, 55, 56
See application file for complete search history.

(56) References Cited

U.S. PATENT DOCUMENTS

| | | |
|---|---|---|
| 3,493,460 A | 2/1970 | Windecker |
| 3,816,610 A | 6/1974 | Lusby |
| 4,104,374 A | 8/1978 | Reuther et al. |
| 4,122,203 A | 10/1978 | Stahl |
| 4,400,298 A | 8/1983 | Boocock et al. |
| 4,564,554 A | 1/1986 | Mikuski |
| 4,688,349 A | 8/1987 | Renth |
| 5,270,108 A | 12/1993 | Savoy |

FOREIGN PATENT DOCUMENTS

| | | |
|---|---|---|
| CA | 1005202 | 2/1977 |

OTHER PUBLICATIONS

The "Mineral Kernite" article, 1997–2000, 2 pages, Bates, *Fine Minerals* on line Mineral Gallery.*

Benning, Calvin J., _Plastic Foams. The Physics and Chemistry of Product Performance and Process Technology_ vol. 2. John Wiley and Sons New York, 1969.

Brown, A. W. A., _Insect Control by Chemicals_. John Wiley & Sons, Inc. : New York, 1951.

Modern Plastics Encyclopedia 1985–1986. McGraw–Hill, Inc.: New York, 1985 trans Springer–Verlag: Berlin, 1986.

Ong, E R de, Chemistry and Uses of Pesticides. Reinhold Publishing Corp.: New York, 1956.

Teach, William C and George C. Kiessling, Polystyrene. Reinhold Publishing Corporation: New York, 1960.

Torgeson, Dewayne C , Ed , Fungicides: An Advanced Treatise Academic Press New York, 1967.

USPTO Document Notice of Non–Compliance of Information Disclosure Statement.

"The Mineral Colemanite" from website: http://mineral galleries com/carbonat/colemani/colemani.htm.

"The Mineral Ulexite" from website. http://mineral.galleries com/carbonat/ulexite/ulexite.htm.

* cited by examiner

*Primary Examiner*—Hai Vo

(57) ABSTRACT

An insulated building panel for use in residential or commercial construction comprising a core of expanded polystyrene (EPS) bonded to at least two exterior skins of oriented strand board by a urethane laminating adhesive and treated with a sodium borate, such as disodium octaborate tetrahydrate, to preserve and protect the building panels from attack by many types of insects, molds, and fungi is disclosed. In an alternative embodiment, EPS for a variety of construction and insulating uses so protected are disclosed.

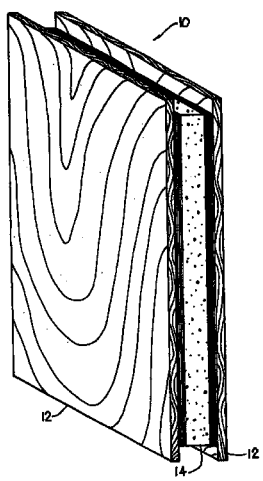

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1-9 are cancelled.

* * * * *